United States Patent
Pedrazzini

(10) Patent No.: US 9,964,554 B2
(45) Date of Patent: May 8, 2018

(54) AUTOMATION MODULE FOR THE MANUAL INTRODUCTION AND PICK UP OF BIOLOGICAL SPECIMENS TO BE URGENTLY INTERFACED WITH A TESTING MODULE FOR LABORATORY DIAGNOSTICS

(71) Applicant: Inpeco Holding Ltd., Qormi (MT)

(72) Inventor: Gianandrea Pedrazzini, Paradiso (CH)

(73) Assignee: INPECO HOLDING LTD., Qormi (MT)

( * ) Notice: Subject to any disclaimer, the term of this patent is extended or adjusted under 35 U.S.C. 154(b) by 0 days. days.

(21) Appl. No.: 14/416,792

(22) PCT Filed: Jul. 18, 2013

(86) PCT No.: PCT/EP2013/065217
§ 371 (c)(1),
(2) Date: Jan. 23, 2015

(87) PCT Pub. No.: WO2014/016199
PCT Pub. Date: Jan. 30, 2014

(65) Prior Publication Data
US 2015/0212103 A1    Jul. 30, 2015

(30) Foreign Application Priority Data

Jul. 25, 2012 (IT) .............................. MI2012A1293

(51) Int. Cl.
*G01N 35/04* (2006.01)
*G01N 35/00* (2006.01)

(52) U.S. Cl.
CPC ....... *G01N 35/00732* (2013.01); *G01N 35/04* (2013.01); *G01N 2035/00752* (2013.01); *G01N 2035/0406* (2013.01); *G01N 2035/0467* (2013.01)

(58) Field of Classification Search
CPC ............. G01N 35/00732; G01N 35/04; G01N 2035/00752; G01N 2035/0406; G01N 2035/0467; G01N 2035/0472
See application file for complete search history.

(56) References Cited

U.S. PATENT DOCUMENTS

| 5,623,415 | A | * | 4/1997 | O'Bryan | G01N 35/021 |
| | | | | | 198/617 |
| 5,941,366 | A | * | 8/1999 | Quinlan | B65G 17/002 |
| | | | | | 198/465.1 |
| 6,024,204 | A | * | 2/2000 | van Dyke, Jr. | G01N 35/04 |
| | | | | | 198/379 |

(Continued)

FOREIGN PATENT DOCUMENTS

WO          96/25712 A1    8/1996

*Primary Examiner* — Natalie Huls
(74) *Attorney, Agent, or Firm* — Jacobson Holman, PLLC.

(57) ABSTRACT

There is described an automation module for the manual introduction and pick up of biological specimens to be directly urgently interfaced with a testing module for laboratory diagnostics, comprising a pair of main lanes and one of secondary lanes on which carrying devices travel for carrying tubes containing said biological specimens. The automation module is provided with separate points for the introduction and the pickup of said tubes into/from said carrying devices, said points being along the secondary lane opposite to that interfaced with said testing module.

2 Claims, 3 Drawing Sheets

(56) References Cited

U.S. PATENT DOCUMENTS

| | | | | |
|---|---|---|---|---|
| 6,202,829 | B1* | 3/2001 | van Dyke, Jr. | G01N 35/04 198/349.6 |
| 8,037,993 | B2* | 10/2011 | Pedrazzini | G01N 35/00732 198/394 |
| 8,973,736 | B2* | 3/2015 | Johns | B01D 21/262 198/439 |
| 2010/0300831 | A1* | 12/2010 | Pedrazzini | G01N 35/00732 198/339.1 |
| 2011/0045958 | A1 | 2/2011 | Pedrazzini | |
| 2011/0112683 | A1* | 5/2011 | Pedrazzini | G01N 35/0095 700/218 |
| 2014/0346009 | A1* | 11/2014 | Pedrazzini | B65G 47/46 198/367 |
| 2016/0039615 | A1* | 2/2016 | Otts | B65G 47/71 198/368 |
| 2016/0161520 | A1* | 6/2016 | Pedrazzini | G01N 35/02 198/571 |

* cited by examiner

AUTOMATION MODULE FOR THE MANUAL INTRODUCTION AND PICK UP OF BIOLOGICAL SPECIMENS TO BE URGENTLY INTERFACED WITH A TESTING MODULE FOR LABORATORY DIAGNOSTICS

The present invention relates to an automation module for the manual introduction and pick up of biological specimens to be urgently interfaced with a testing module for laboratory diagnostics.

Nowadays, within the field of automation for laboratory diagnostics, the need of urgently providing to the testing of some biological specimens, carried into tubes along an automation line through dedicated transport devices, is increasingly felt.

Considering an automation system as a whole, apparatus are already known wherein the tubes are stored in large amounts to be released as needed towards the suitable testing modules.

Within such automation systems, a possibility is also known to separate the treatment of so-called routine or ordinary tubes, which follow a normal flow along the system, from those which, on the other hand, have a certain urgency to be treated (STAT, Short Turn-Around Time) based on predetermined devices, since for example the specimen they contain has just been taken from a patient the conditions whereof may be particularly critical and which therefore requires immediate diagnosis and treatment.

To this end, in known systems both types of tubes substantially follow the same path within the automation system, although there is a series of equipment for identifying and routing the tubes which for example allow the urgent ones to be picked up and placed on the automation line before the ordinary ones, or to be passed over along the path or in any case, to reach the testing modules arranged along the system with a sort of "priority". All of this is achieved thanks to the high automation level of the machinery making up the system as a whole.

It is also true that using a fully automated management may often be inconvenient, especially if the specimens are introduced in the automation system through pick up from the typical specimen loading/unloading benches; in fact since the latter need to contain a large amount of tubes, they are bulky by definition (in addition to being very expensive) and thus they cannot be provided in a large number along the system (typically one or two units at most).

It is understood that often, the subject bench may be very distant from some of the testing modules present along the automation line and thus, managing a quick routing of specimens along such distant testing modules may be complicated.

The object of the present invention therefore is to implement an automation module which allows the "immediate" introduction of specimens to be treated with particular urgency, making such an introduction take place in a point of the automation line which is as close as possible to the relevant testing module, i.e., the one that must take delivery of the above specimens for carrying out an immediate processing thereof.

A further object of must be to implement an automation module which allows the quick pick up of the specimen again once the processing thereof by the testing module has ended in order to quickly route it as needed to a new testing module different from the previous one or to dispose of it without uselessly making it travel along the automation system.

According to the invention, this and other objects are achieved by an automation module for the manual introduction and pick up of biological specimens to be urgently interfaced with a testing module for laboratory diagnostics as described in claim 1.

These and other features of the present invention will appear more clearly from the following detailed description of an embodiment thereof, made by way of a non-limiting example with reference to the accompanying drawings, in which.

Figure 1:
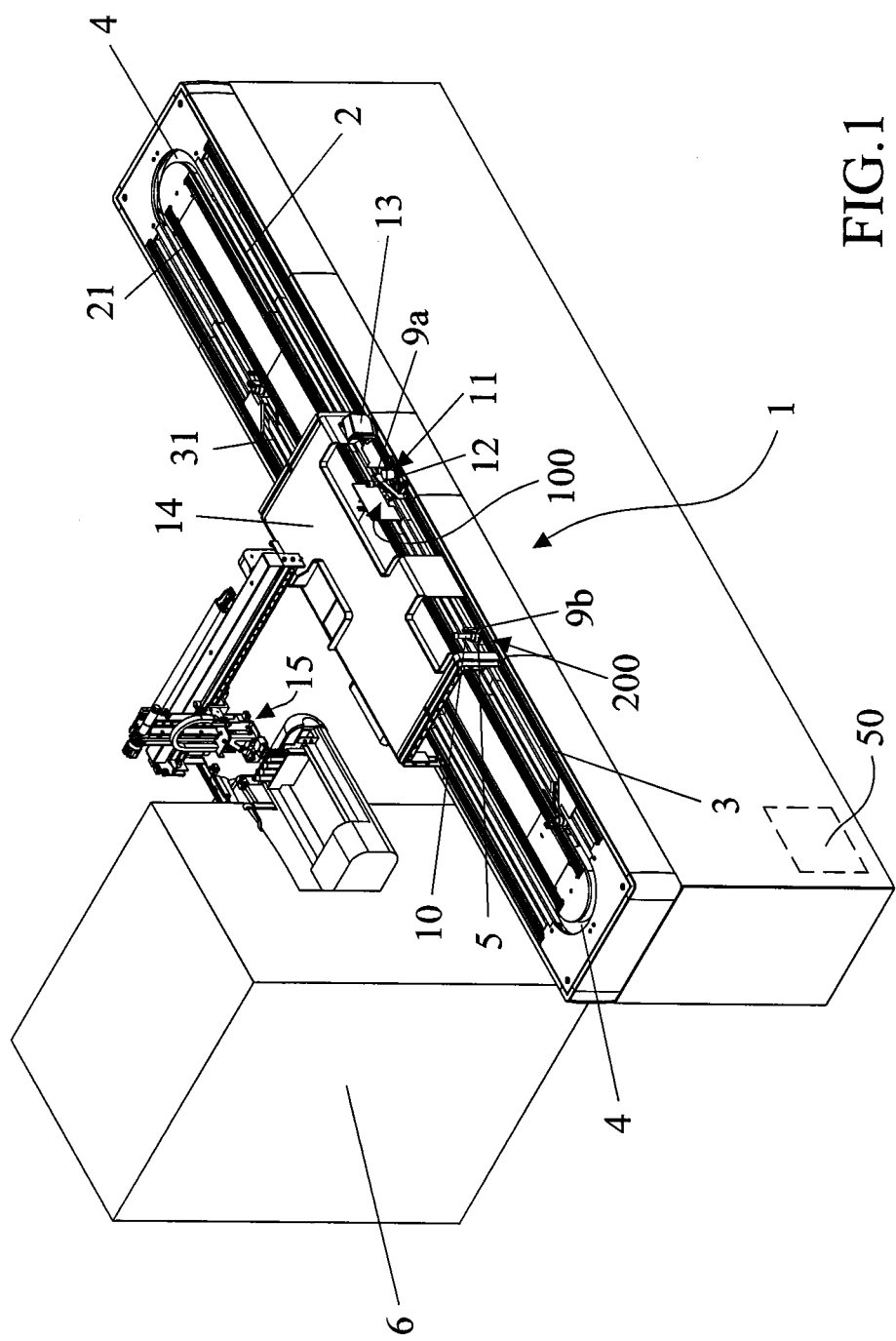
FIG. 1 shows a perspective view of an automation module according to the invention, interfaced with a generic testing module for laboratory diagnostics.

A laboratory automation system comprises a plurality of modules which are assembled to one another in a variable number and according to different configurations for meeting the different requirements of testing laboratories. The modules, next to each other, concur to forming the automation system as a whole. The automation system also comprises testing modules 6 for laboratory diagnostics.

Automation modules 1 (FIG. 1) according to the present invention are intended for the manual introduction and pickup of biological specimens to be directly urgently interfaced with the testing module 6, actually skipping the path that tubes 10 should follow if they were introduced in the automation system through one or more loading/unloading benches.

Each of such modules 1 is provided with two pairs of lanes, in particular a first 2 and a second 21 main lanes and a first 3 and a second 31 secondary lanes, on which carrying devices 5 travel for making the transport of very urgent tubes 10 faster, directly to the testing module 6, following a path which is circumscribed to just module 1 itself, thanks to the presence at both ends of the first 2 and of the second 21 main lanes of two U-shaped turning modules 4 which allow the carrying devices 5, containing or not tubes 10 and continuously circulating along module 1, to directly move from the first main lane 2 along a side to the second main lane 21 along the other side of module 1 and vice versa.

Interfaced with the second secondary lane 31 of module 1, along one of the two larger sides of the same, there is the testing module 6 intended to accommodate biological material specimens and carry out various testing treatments on the same. The interfacing may for example occur, according to the embodiment shown in FIG. 1, by means of a known mechanical device 15 provided with pickup fingers. It is intended to pick up tubes 10 from each carrying device 5 circulating along module 1 for placing them on the testing module 6. Each carrying device 5 contains a single tube 10 so that as soon as the biological specimen of tube 10 is ready, it may be urgently sent along module 1 and hence, directly and urgently to the testing module 6. The opposite operation is carried out at the end of the testing of tubes 10 into module 6, i.e. the testing module 6 places tubes 10, through the mechanical device 15, back again on one of said carrying devices 5 along module 1. It should be noted, as said, that the use of a mechanical device 15 for transferring tubes 10 into the testing module 6 and vice versa from said testing module 6 to the second secondary lane 31 is only one of the possible solutions which may be adopted for interfacing the automation module 1 and the testing module 6 with each other and that therefore, such solution is shown in FIG. 1 for illustration purposes only.

Figure 3:
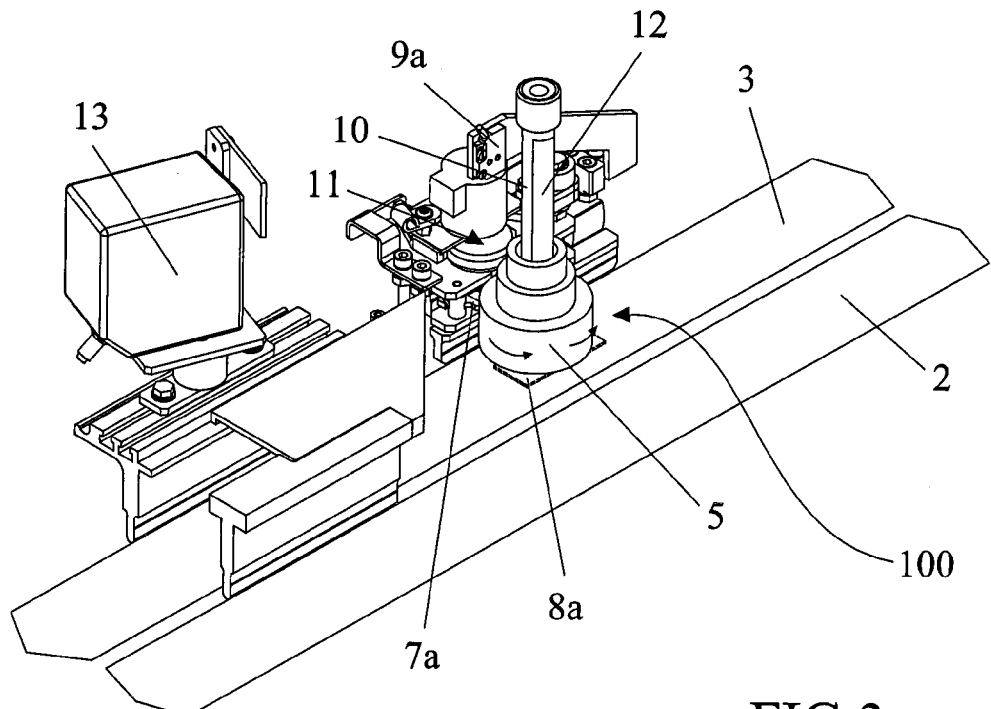
FIG. 3 shows a detail of the specimen introduction point comprised in said automation module.

On the other hand, a specimen introduction point 100 (FIG. 3) comprising a first stopping gate 7a of the carrying devices 5 is provided along the first secondary lane 3 of the other side of module 1, which is associated to a first antenna 8a located beneath the conveyor belt of the secondary lane 3 and intended for detecting the carrying device 5 stopped at the first gate 7a. Moreover, there is a first sensor 9a for detecting a tube 10 contained in the carrying device 5.

Such specimen introduction point 100 further comprises a rotation apparatus 11 of the carrying device 5, provided with a motor, which makes the barcode printed on a label 12 glued onto tube 10 to be read by a barcode reader 13.

Figure 2:
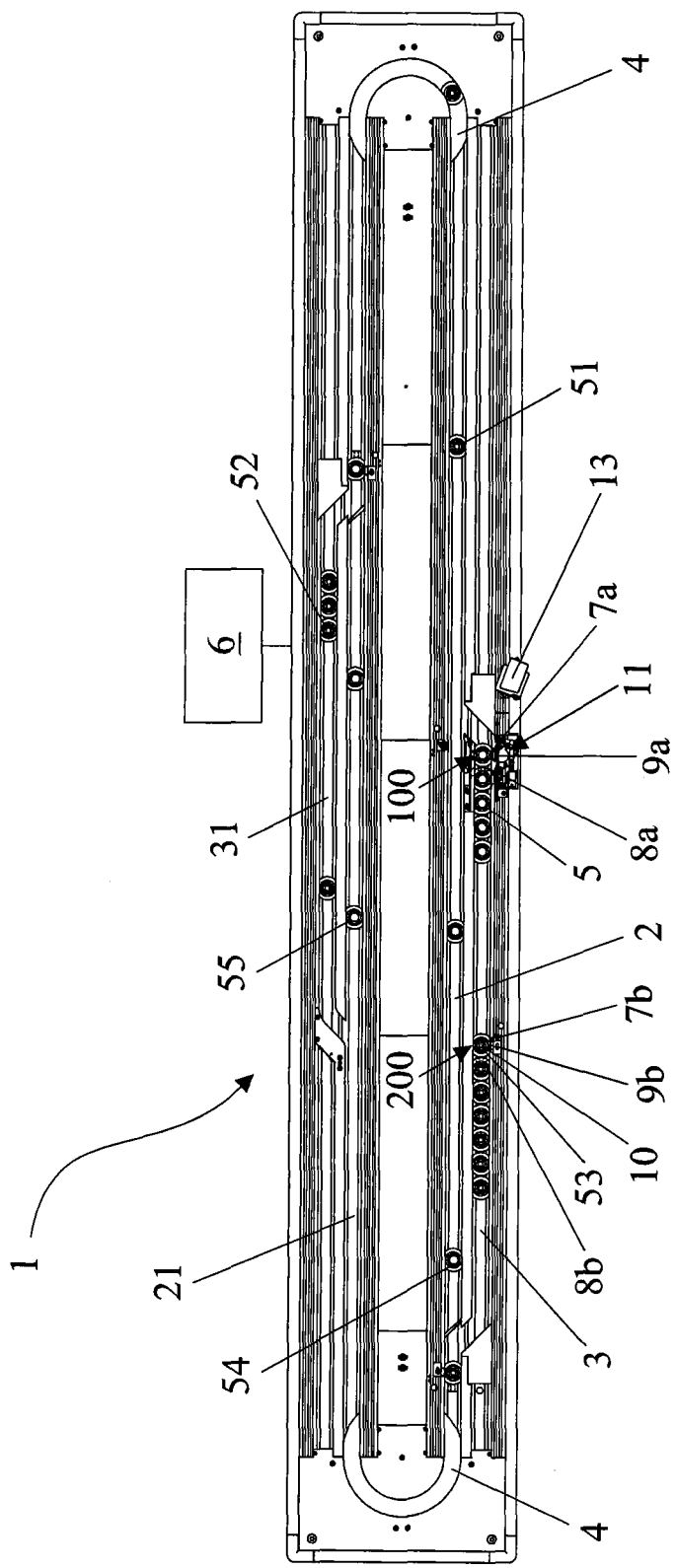
FIG. 2 shows a plan top view of the automation module in FIG. 1, having removed the cover of the same.
Figure 4:
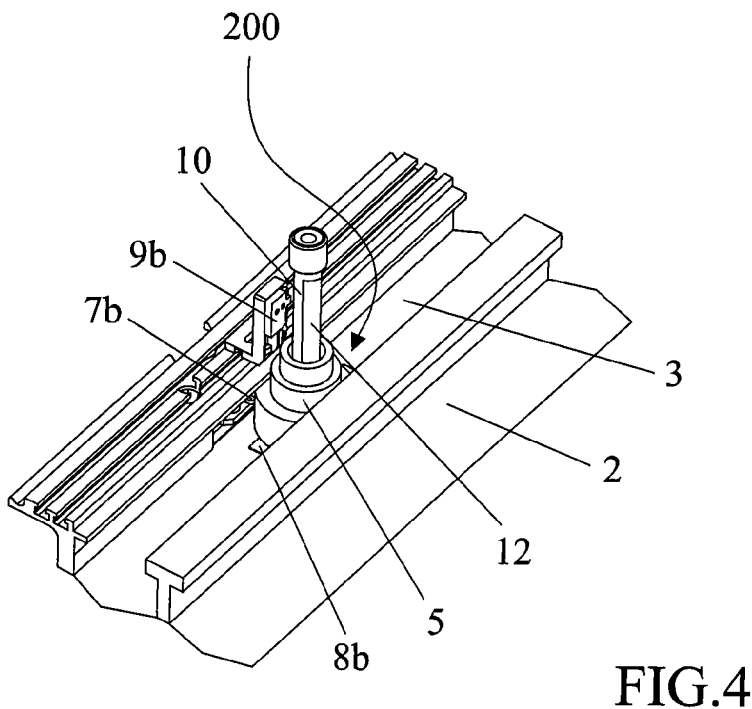
FIG. 4 shows a detail of the specimen pick up point comprised in said automation module.

Still on the same side of module 1 and along the same first secondary lane 3 (more leftwards, in the representations in FIGS. 1 and 2) there is a specimen pickup point 200 (FIG. 4) which comprises a second stopping gate 7b, a second antenna 8b and a second sensor 9b for detecting a tube 10, with the same functions already described above. The pickup point 200 is before the introduction point 100 in a sequence, i.e. more leftwards than the introduction point 100, since the carrying devices 5 move from the left rightwards along the first secondary lane 3 so that said sequence is adapted to make the carrying devices 5 move from the pickup point 200 to the introduction point 100. The vicinity on the same first secondary lane 3 between the introduction point 100 and the pickup point 200 of tubes 10 advantageously allows a quick action by the operator who must first urgently introduce tubes 10 for routing them directly towards the testing module 6 and have them tested in a very short time, and must then quickly and urgently recover the tested tubes 10, and he/she can do this in the immediate vicinity of the introduction point 100; in this way, he/she never needs to move, i.e. follow the automation system path.

Module 1 may be surmounted by a cover 14 (FIG. 1), suitably open at the specimen introduction point 100 and at the specimen pickup point 200, where the operator must be able to manually act according to what will be described even better hereinafter.

Module 1 typically accommodates biological material specimens to provide to the testing module 6 as quickly as possible. This may be necessary in particularly urgent situations where it is not possible to wait for the above specimens to follow the ordinary flow path along the whole system automation line, since the particularly urgent situation requires an immediate testing and thus diagnosis of the same. Normally, the testing module 6 tests tubes 10 coming from the automation system. Module 1 is made for making the very urgent tubes 10 skip the winding path of the automation system by directly and urgently sending them to the testing module 6. The very urgent tubes 10 are not loaded onto the automation system since they require even quicker testing times for extremely urgent reasons. Module 1 allows the introduction, testing and pick up of tubes 10 in very short times, with great quickness and keeping the very urgent tubes 10 into module 1 and the testing module 6. In this way, the testing and after the testing, the quick pick up of the very urgent tubes 10 from module 1 only at the pickup point 200, which is in the immediate vicinity of the introduction point 100, much faster, thus making the use of said module 1 even by a single operator extremely advantageous.

The introduction of specimens into module 1 takes place manually, by the operator, at the specimen introduction point 100. Module 1 is set up to always make empty carrying devices (FIG. 2) available at point 100 where the operator can introduce, one at a time, tubes 10 containing biological material just taken from a patient and to be urgently tested. Each tube 10 has been suitably labeled in a previous step with a label 12 provided with a patient identification barcode and with the number and type of test to be made on the specimen contained therein.

Of course, a tube 10 is first introduced in the carrying device 5 already stopped at the first stopping gate 7a (and meanwhile detected by antenna 8a) at the introduction point 100, and thereafter any other queued carrying devices 5 are progressively filled.

At this point, once the presence of tube 10 has been detected by the first sensor 9a (FIG. 3), the rotation of the carrying device 5 is started by means of the rotation apparatus 11, which allows the barcode reader 13 to detect the barcode present on label 12 applied onto tube 10.

The automation module 1 further comprises a central control unit 50 (FIG. 1), which, once the information from the barcode reader 13 has been received, checks whether tube 10 just picked up actually needs to be routed to the testing module 6. Once such a confirmation has been obtained, the first stopping gate 7a retracts, so that the carrying device 51 with tube 10 (FIG. 2) is sent along the first main lane 2 of module 1.

Once the U-shaped turning module 4 has been surpassed, the carrying device 52 provided with tube 10 reaches the second main lane 21 on the side of module 1 interfaced with the testing module 6, and in particular it is deviated along the second secondary lane 31 of the same, which is adapted to act as preferential testing lane for said carrying devices 5. Here, the pickup takes place for example by means of a mechanical gripping device 15 of tube 10 and the placement of the same in the testing module 6. As already mentioned, the interfacing methods between module 1 and the testing module 6 may be multiple according to the shape of the latter and alternative devices may be provided as compared to the mechanical gripping device 15.

Thereafter, the testing module 6 then carries out the actual testing treatment on the specimen.

The operation is repeated in a cascade for the specimens introduced in the introduction point 100 subsequent to the first one, thus favoring the sequential release from the first stopping gate 7a along the first secondary lane 3 and then along the first main lane 2, and the sequential arrival on the other side of module 1 along the second main lane 21 and then along the second secondary lane 31, at the testing module 6.

The carrying device 5 just deprived of tube 10, since it has been loaded into the testing module 6, may be immediately released onto the second secondary lane 31 for returning onto the second main lane 21 and then, surpassing the next U-shaped turning module 4, along the other side of module 1 on the first main lane 2. However, the case may happen in which the carrying device 5 is not actually released since the testing module 6, in addition to accommodating the new tube 10, is also about to eject a previously introduced and thus already tested one; in such a case, the carrying device 5 just freed of one tube 10 is kept locked so as to shortly accommodate a different one, unloaded from the testing module 6.

The decision as to whether to release the carrying device 5 is a prerogative of the central control unit 50 which, by receiving the information of sensors 9a, 9b, knows the release time of each tube 10 from the testing module 6 and can therefore manage the whole.

The either empty or full carrying device 5 returns along the second main lane 21 (for example by means of a known automatic return device) and, once the U-shaped turning module 4 (on the left in FIG. 2) has been surpassed, it is along the first main lane 2. Said first 2 and second 21 main lanes are adapted to keep said carrying devices 5 in continuous circulation on a waiting path to be then routed towards the secondary lanes 3, 31. The carrying device 5 may either be diverted or not from the first main lane 2 in the direction of the specimen pickup point 200 along the first secondary lane 3, or it may remain on the waiting path along the first main lane 2 and the second main lane 21.

In particular, if the carrying device 53 (FIG. 2) contains a tube 10 in output from the testing module 6, it is certainly diverted towards the pickup point 200 to set up in columns with other carrying devices 5 at said pickup point 200 in the first secondary lane 3, so that tube 10 is as soon as possible manually picked up by the operator. This happens when the carrying device 53 stops at the second stopping gate 7b and tube 10 is detected by the second tube presence sensor 9b; after such a detection, tube 10 can finally be picked up by the operator.

Of course, in case of the sequential arrival of multiple carrying devices 5 containing tested tubes 10, they are put into columns forming a queue in the vicinity of the specimen pickup point 200; it is essential for the operator to wait for each carrying device 5 to reach the first position along the queue, at the second stopping gate 7b, before picking up the relative tube 10. This is to allow the tube presence sensor 9b to carry out the suitable detection, one at a time, on each tube 10 which is about to be manually picked up, so as to consistently close the processing cycle of each of them into the automation module 1.

Each carrying device 5 emptied in the specimen pickup point 200 is then released through the retraction of the stopping gate 7b and then returns at the specimen introduction point 100 adding up to the queue, optionally already present, of certainly empty carrying devices 5.

In general, empty carrying devices 5 should never be missing at the specimen introduction point 100 to cope with any sudden needs of introduction of new urgent specimens along module 1.

The latter need of always having empty carrying devices 5 available at point 100 also affects the routing or not of the incoming empty carrying device 5 along the first secondary lane 3 from the opposite side of module 1, i.e. that interfacing with the testing module 6.

In fact, once surpassed the U-shaped turning module 4 on the left (FIG. 2), the carrying device 5 can in any case be diverted along the first secondary lane 3, even if it is empty, if at that time at the specimen pickup point 200 there is no carrying device 5 and if at the same time there is also a temporary lack of queued carrying devices 5 at the specimen introduction point 100. In fact, in this way, since the second sensor 9b does not detect the presence of any tube and therefore it is not necessary to wait for the operator to manually pick up anything, the carrying device 5 is released almost immediately from the stopping gate 7b and queues up at the specimen introduction point 100, thus remedying the temporary (partial or even total) lack mentioned above.

Vice versa, there is no need anymore to divert an empty carrying device 5 along the first secondary lane 3 if a queue of full carrying devices 5 is already present at the specimen pickup point 200. In fact the latter, once the respective tube 10 has been picked up at the second stopping gate 7b, go into the queue at the specimen introduction point 100, obviating any lacks of carrying devices 5 at point 100. Therefore, in this case, the empty carrying device 54 (FIG. 2) is not diverted and continues along the first main lane 2 and along the second main lane 21; this until there is the need to route it along the second secondary lane 31 to interface with the testing module 6, so as to accommodate a tube 10 therefrom, or divert it to a subsequent round, still empty, along the first secondary lane 3 of the other side since, for example, the queue at point 200 meanwhile has cleared out.

The queue of empty carrying devices 5 stopped at the specimen introduction point 100 cannot exceed, for space reasons along the secondary lane 3, a predetermined number of such carrying devices 5, which may optionally be set as desired according to the needs; for this reason, if they keep on arriving at point 100 since they are released from the second stopping gate 7b and such an allowed number is exceeded, carrying devices 55 are in turn released from point 100 even if they are not filled with new specimens to be tested, only for clearing out the queue formed at the introduction point 100. Such carrying devices 55 are temporarily circulated along the waiting path of the main lanes 2, 21, carrying out a continuous loop, i.e. a continuous circulation from which they are called back as needed.

Another case which contemplates the release of carrying devices 5 from the specimen introduction point 100 without actually being filled with tubes 10, is that in which tubes 10 are about to be unloaded from the testing module 6 and there is a lack (if not total absence) of carrying devices 5 which may accommodate such tubes 10. To this end, the carrying devices 5 are thus called back from the specimen introduction point 100 and they add up to the queue along the second secondary lane 31 in the vicinity of the interface between module 1 and the testing module 6. The carrying devices 5 that leave point 100 are again replaced by those released from point 200 as soon as the operator frees them of the respective tube 10.

As is well understood, the overall management of the release or restraint of the carrying devices 5 along the whole module 1 (and thus both on the side with points 100 and 200 and on the opposite side) is again a responsibility of the central control unit 50.

Ideally, the result achieved at the end of an operating cycle on multiple specimens, started with the consecutive introduction of the same from point 100, is the removal of the same, again in a sequence, from point 200, so that only empty carrying devices 5 finally remain circulating along module 1. Of course, this is an ideal solution because based on the contingent needs, the introduction of new tubes 10 from point 100 may not follow a regular frequency; thus, multiply cycles may overlap each other, so that at the end of the processing on a series of specimens, other new ones have already been inserted and are thus circulating along module 1.

One of the innovative aspects of the invention therefore is to provide, within the field of laboratory diagnostic automation, for the presence of one or more modules 1 substantially isolated from the rest of the automation system, each of which directly interfaces with a specific testing module 6; this is functional to the manual, direct and immediate introduction, by an operator, of tubes 10 containing biological material to be processed very urgently and thus to quickly and directly route to the testing module 6.

At the end of the testing carried out by module 6, tube 10 returns along module 1 and can then be picked up, still manually, by an operator, for example to be carried to a subsequent and similar module 1 intended to interface with a different testing module 6. The pickup point 200 and the introduction point 100 are at a very short distance from each other since they are adapted to be handled also by a single human operator.

In the practice, it has been seen that the equipment as described can achieve the intended objects, overcoming the drawbacks of the prior art, where a biological material specimen is often introduced or picked up along the automation through one or more loading/unloading benches located at predetermined points along the automation system.

Firstly, these benches do not immediately route the specimens along the system lanes, since the introduction of each tube into the related carrying device, i.e. along the automation path line, only occurs after the selective pickup of the tubes themselves by, for example, a mechanical gripping device.

Moreover, such benches are particularly bulky and by virtue of this, few units may certainly be present in an automation system. Therefore, in the prior art, tubes 10 may also be at very distant points from a specific testing module 6 and if there is the need to urgently carry out a testing by means of such a specific module 6, on a specimen just introduced by means of such benches, the specimen may be very far from the subject testing module 6 and thus, a long time may pass before it reaches the same. This certainly contributes to a waste of precious time, which is even more crucial if the conditions of the patient to whom the biological specimen to be tested belongs are critical.

On the other hand, thanks to the present invention, the specimen of tube 10 just tested advantageously returns in a short time to the operator who can quickly carry it in the vicinity of a further module 1, in turn interfaced with a further testing module 6, or dispose of it. This prevents what happens in the prior art, i.e. that the specimen of tube 10 must cover a long path along the automation line for reaching such further testing module 6 or a bench again with a plurality of tubes 10 wherein it must be unloaded.

Several changes and variations may be made to the invention thus conceived, all falling within the scope of the inventive concept.

In the practice, the materials used as well as shapes and sizes, may be any, according to the requirements.

The invention claimed is:

1. An automation module for the manual introduction and pick up of biological specimens to be directly interfaced with a testing module for laboratory diagnostics of an automation system, wherein
   said automation module comprises a first and a second main lane, two U-shaped turning modules and a first and a second secondary lane on which single-tube carrying devices travel, each single-tube carrying device being able to contain a tube for said biological specimens,
   the first secondary lane being provided with a specimen manual introduction point to introduce said tubes into said single-tube carrying devices, and a specimen manual pickup point to remove said tubes from said single-tube carrying devices,
   the specimen manual pickup point and the specimen manual introduction point being in a sequence along the same first secondary lane,
   the specimen manual pickup point being before the specimen manual introduction point to make the single-tube carrying device move from the specimen manual pickup point to the specimen manual introduction point,
   said specimen manual pickup point being after diverting the single tube carrying device with the tube to be manually picked-up, from the first main lane to the first secondary lane, said specimen manual introduction point being before returning the single tube carrying device with the tube manually introduced, from the first secondary lane to the first main lane,
   the first and the second main lanes and said two U-shaped turning modules, present at the ends thereof, being adapted to keep said single-tube carrying devices in continuous circulation along a waiting path in order for being routed towards the secondary lanes,
   said second secondary lane being directly interfaced with said testing module and suitable for serving as preferential testing lane for said single-tube carrying devices,
   said single-tube carrying devices outgoing from the testing module being suitable for queuing along the first secondary lane at the specimen manual pickup point,
   said specimen manual introduction point comprising a first stopping gate, a first antenna intended for detecting said single-tube carrying devices, a first sensor for detecting said tubes and a rotation apparatus provided with a motor which provides the rotation of said single-tube carrying devices for detecting a barcode, printed on labels glued on said tubes, by a barcode reader,
   said specimen manual pickup point comprising a second stopping gate, a second antenna intended for detecting said carrying devices, and a second sensor for detecting said tubes.

2. The automation module according to claim 1, wherein it comprises a central control unit for managing the routing of said single-tube carrying devices along the whole module.

* * * * *